(12) United States Patent
Alberto et al.

(10) Patent No.: US 10,384,023 B2
(45) Date of Patent: Aug. 20, 2019

(54) SELECTIVE RAMPING OF THERAPEUTIC PRESSURE IN A PATIENT BREATHING APPARATUS

(75) Inventors: Leonardo Alberto, Lake Forest, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 194 days.

(21) Appl. No.: 13/566,902

(22) Filed: Aug. 3, 2012

(65) Prior Publication Data

US 2014/0034055 A1 Feb. 6, 2014

(51) Int. Cl.
*A61M 16/10* (2006.01)
*A61M 16/00* (2006.01)
*A61M 16/06* (2006.01)

(52) U.S. Cl.
CPC .... *A61M 16/0051* (2013.01); *A61M 16/0003* (2014.02); *A61M 16/0069* (2014.02); *A61M 16/021* (2017.08); *A61M 16/024* (2017.08); *A61M 16/10* (2013.01); *A61M 16/0066* (2013.01); *A61M 16/06* (2013.01); *A61M 16/105* (2013.01); *A61M 16/107* (2014.02); *A61M 2016/0015* (2013.01); *A61M 2016/0027* (2013.01); *A61M 2205/3331* (2013.01); *A61M 2205/42* (2013.01); *A61M 2205/502* (2013.01); *A61M 2205/505* (2013.01); *A61M 2205/581* (2013.01)

(58) Field of Classification Search
CPC .......... A61M 16/0051; A61M 16/0057; A61M 2230/005

USPC .............. 128/204.6, 200.24, 200.11, 204.18, 128/204.19, 204.21, 204.22, 204.23, 128/204.29, 205.11, 207.14, 207.18
See application file for complete search history.

(56) References Cited

U.S. PATENT DOCUMENTS

| | | | |
|---|---|---|---|
| 5,239,995 A | 8/1993 | Estes et al. |
| 5,503,146 A | 4/1996 | Froehlich et al. |
| 5,682,878 A | 11/1997 | Ogden |
| 6,401,713 B1 | 6/2002 | Hill et al. |

(Continued)

OTHER PUBLICATIONS

Notification of Transmittal of the International Search Report and the Written Opinion of the International Searching Authority dated Nov. 29, 2013; 13 Pages.

*Primary Examiner* — Tu A Vo
(74) *Attorney, Agent, or Firm* — Stetina Brunda Garred and Brucker; Mark B. Garred (57) ABSTRACT

A respiratory assistance device includes a patient interface for coupling to a patient respiratory passageway, and a selectively regulated therapeutic gas flow source in pneumatic communication with the patient over the patient interface. A ramping controller is connected to the therapeutic gas flow source and is receptive to inputs of a prescription pressure level, an initial pressure level, a total ramp duration, and a numeric value corresponding to a ramping duration. Therapeutic gas flow at an initial pressure level is regulated for a ramp delay duration reciprocal to the ramping duration relative to the total ramp duration. The ramping controller incrementally increases therapeutic gas flow to the prescription pressure level from a ramp start time to a ramp end time at a delivery pressure increase rate derived from the numeric value of the ramping duration and the total ramp duration.

20 Claims, 5 Drawing Sheets

(56) References Cited

U.S. PATENT DOCUMENTS

| | | | |
|---|---|---|---|
| 6,427,689 B1 | 8/2002 | Estes et al. | |
| 6,581,595 B1 * | 6/2003 | Murdock | A61B 5/083 |
| | | | 128/204.18 |
| 7,469,698 B1 * | 12/2008 | Childers et al. | 128/204.23 |
| 8,011,366 B2 | 9/2011 | Knepper | |
| 8,276,585 B2 * | 10/2012 | Buckley et al. | 128/204.23 |
| 2002/0053345 A1 * | 5/2002 | Jafari | A61M 16/00 |
| | | | 128/204.23 |
| 2004/0187870 A1 * | 9/2004 | Matthews et al. | 128/204.22 |
| 2005/0166920 A1 | 8/2005 | Delache et al. | |
| 2006/0118112 A1 * | 6/2006 | Cattano et al. | 128/204.21 |
| 2006/0249153 A1 * | 11/2006 | DeVries | A61M 16/0057 |
| | | | 128/204.18 |
| 2007/0028920 A1 * | 2/2007 | Acker | A61M 16/0051 |
| | | | 128/204.21 |
| 2007/0163590 A1 * | 7/2007 | Bassin | A61M 16/00 |
| | | | 128/204.23 |
| 2008/0053441 A1 * | 3/2008 | Gottlib | A61M 16/0051 |
| | | | 128/204.23 |
| 2008/0178880 A1 * | 7/2008 | Christopher | A61M 16/0051 |
| | | | 128/204.23 |
| 2008/0185009 A1 * | 8/2008 | Choncholas | A61M 16/00 |
| | | | 128/897 |
| 2009/0013999 A1 * | 1/2009 | Bassin | 128/204.18 |
| 2009/0126731 A1 * | 5/2009 | Dunsmore | A61M 16/0096 |
| | | | 128/203.12 |
| 2009/0293875 A1 | 12/2009 | Kwok et al. | |
| 2010/0011307 A1 * | 1/2010 | Desfossez et al. | 715/764 |
| 2010/0078024 A1 | 4/2010 | Andrieux et al. | |
| 2010/0186741 A1 * | 7/2010 | Aylsworth et al. | 128/203.29 |
| 2012/0017909 A1 * | 1/2012 | Porges | A61M 16/12 |
| | | | 128/205.25 |

\* cited by examiner

SELECTIVE RAMPING OF THERAPEUTIC PRESSURE IN A PATIENT BREATHING APPARATUS

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the treatment of respiratory and cardiovascular conditions, and more particularly, to methods and systems for continuous positive airway pressure (CPAP) therapy and the selective ramping of therapeutic pressure in a patient breathing apparatus.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient's airway to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Various improvements have been developed that reduce positive pressure flow to the patient during the expiratory phase, thereby reducing resistance to the patient's breathing efforts and patient discomfort. Further refinements that recognize the minimal flow and pressure toward the end of the patient's expiratory phase and responsively reduce the delivery of positive pressure have also been contemplated.

Earlier patient breathing assistance devices tended to be uncomfortable to use, not only for its bulkiness with respect to the patient interface or mask, but as mentioned above, the reduced accuracy of the control algorithms that resulted in the misapplication of patient pressure. With these issues being resolved, or at least being significantly improved upon, what was previously prescribed only for the more severe cases of sleep apnea in which the benefits of treatment outweighed the significant discomfort is now useful for treating a wider spectrum of sleep apnea conditions. Further cost reductions were possible with the elimination of expensive flow sensors and control systems based thereon in favor of pressure sensor based systems such as that described in U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein.

Notwithstanding the increased availability of CPAP devices for home use as a result of these technical improvements and cost-saving measures, ensuring patient compliance with the prescribed treatment remains a challenge. One of the most frequent complaints, and the cause of non-compliance, is the discomfort associated with the application of pressure against the respiratory system of the patient. The additional work required during spontaneous exhalation and the forcing of air during spontaneous inhalation, may cause a suffocating sensation. Even minimal levels of pressure may be distracting enough to a patient such that merely falling asleep becomes difficult. Once in a state of sleep, however, the application of full therapeutic pressure (properly prescribed in accordance with the patient's condition) generally does not interrupt the patient's sleeping state.

In order to minimize patient discomfort during the pre-sleep state, breathing assistance devices incorporate ramping, where delivered pressure is gradually increased over a set time period. There are a variety of delivery pressure increase curves, also referred to as ramp paths, which may be implemented by the device. These include linear ramp paths, a curved ramp path that increases delivery pressure at a higher rate in the initial time period of the ramp duration, a curved ramp path that increases delivery pressure at a higher rate in the later time period of the ramp duration, and so forth. In some devices, it is possible for the patient to select between multiple available ramp paths depending preference.

Despite such improvements, even the low levels of pressure being delivered at the beginning of the ramp, which are fractions of the full therapeutic pressure, may be enough to cause discomfort for some patients. Accordingly, there is a need in the art for the selective ramping of therapeutic pressure in a patient breathing apparatus.

BRIEF SUMMARY

The present disclosure contemplated the selective ramping of therapeutic gas delivery to a patient with a respiratory assistance device. One embodiment is directed to a method of selective ramping, which may include a step of receiving a prescription pressure level, an initial pressure level, a total ramp duration and a numeric value corresponding to a ramping duration. Thereafter, the method may include generating a ramp delay value from the numeric value corresponding to the ramping duration relative to the total ramp duration. Then, there may be a step of generating a delivery pressure increase rate between the initial pressure level and the prescription pressure level. The delivery pressure increase rate may be based upon a ramp start time and a ramp end time, and may further be derived from the ramping duration and the total ramp duration. The method may include receiving a treatment initiation command following the patient being pneumatically coupled to the respiratory assistance device over a patient interface. Then, the method may continue with initiating gas delivery from the respiratory assistance device to the mask at the initial pressure level. This may be in response to receiving the treatment initiation command. The gas delivery at the initial pressure level may continue for the ramp delay duration. Furthermore, there may be a step of increasing gas pressure from the respiratory assistance device to the mask at the derived delivery pressure increase rate from the ramp start time to reach the prescription pressure level by approximately the ramp end time. The foregoing method may also be embodied as a series of executable instructions stored on and read from a non-transitory program storage medium by a data processor in the respiratory assistance device. Yet another embodiment is directed to a respiratory assistance device for a patient. The device may include a patient interface for coupling to a patient respiratory passageway. Additionally, there may be a selectively regulated therapeutic gas flow source in pneumatic communication with the patient over the patient interface. The device may also include a ramping controller that is connected to the therapeutic gas flow source and may be receptive to inputs of a prescription pressure level, an initial pressure level, a total ramp duration, and a numeric value corresponding to a ramping duration. The ramping controller may regulate therapeutic gas flow at an initial pressure level for a ramp delay duration reciprocal to the ramping duration relative to the total ramp duration. The ramping controller may also incrementally increase therapeutic gas flow to the prescription pressure level from a ramp start time to a ramp end time at a delivery pressure increase rate that may be derived from the numeric value of the ramping duration and the total ramp duration.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the presently disclosed selective ramping of therapeutic pressure in a patient breathing apparatus, and is not intended to represent the only forms that may be developed or utilized. Generally, the apparatus delivers breathing gas to a patient for the treatment of obstructive sleep apnea (OSA) and other cardio-pulmonary conditions, and selectively augments and relieves pressure throughout the breathing cycle. The description sets forth the various functions in connection with the illustrated embodiments, but it is to be understood, however, that the same or equivalent functions may be accomplished by different embodiments that are also intended to be encompassed within the scope of the present disclosure. It is further understood that the use of relational terms such as first and second and the like are used solely to distinguish one entity from another without necessarily requiring or implying any actual such relationship or order between such entities.

Figure 1:
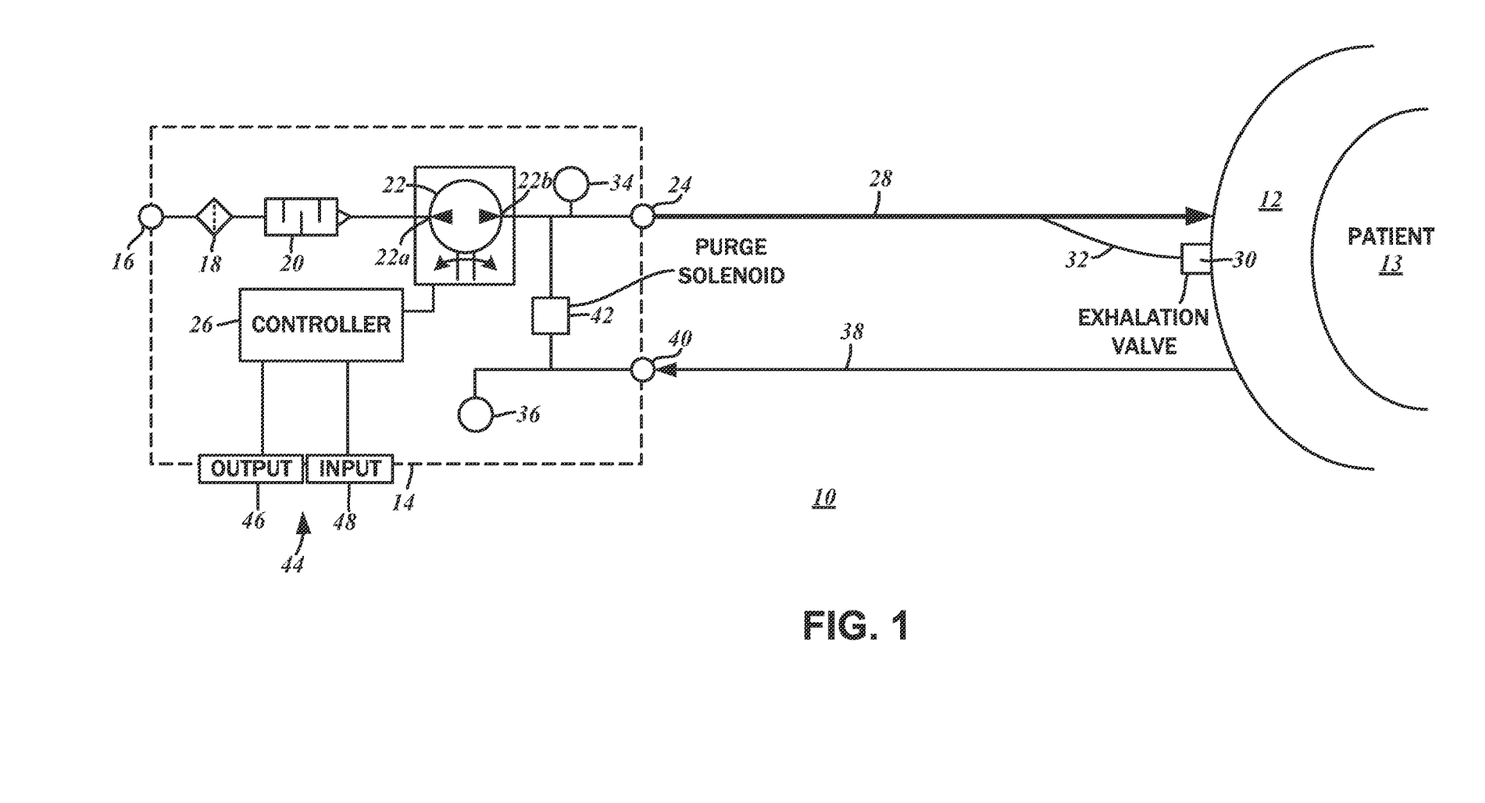
FIG. 1 is a block diagram showing the various components of a CPAP apparatus in accordance with various embodiments of the present disclosure including a typical ventilation unit, a patient ventilation mask, and gas passage conduits.

The block diagram of FIG. 1 illustrates an exemplary respiratory assistance device 10 in which various embodiments of the present disclosure may be implemented. There is a mask or patient ventilation interface 12, and a ventilation unit 14. The following disclosure will make reference to the patient ventilation interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. One possible mask 12 is disclosed in U.S. patent application Ser. No. 13/411,348 entitled VENTILATION MASK WITH INTEGRATED PILOTED EXHALATION VALVE filed Mar. 2, 2012, now issued U.S. Pat. No. 8,844,533, and U.S. patent application Ser. No. 13/411,407 entitled VENTILATION MASK WITH INTEGRATED PILOTED EXHALATION VALVE, filed Mar. 2, 2012, now issued U.S. Pat. No. 8,839,791, the disclosures of which are hereby incorporated by reference in their entireties herein. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements various methods of CPAP treatment such as those disclosed in the aforementioned co-pending U.S. patent application Ser. No. 13/411,257.

The flow of breathing gas that is output from the ventilation source 22 is passed through the outlet port 24 to a gas conduit 28 that is in coupled to the aforementioned patient ventilation interface 12. The gas conduit 28 is understood to be a plastic tube having a predetermined inner diameter such as 22*mm* or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted exhalation valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In order to ascertain such pressure differentials, the presently contemplated respiratory assistance device 10 includes dual pressure sensors, including a source pressure sensor 34 and a patient interface sensor 36. The source pressure sensor 34 is disposed within the ventilation unit 14, and monitors the pressure at the outlet port 22*b*. The patient interface pressure sensor 36 is also physically disposed within the ventilation unit 14, but is in direct gas flow communication with the patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

As indicated above, the sequence and timing of delivering gas flow to the patient 13 are governed by the specific treatment modalities that utilize feedback data from the pressure sensors 34, 36. The setting of options relating to the treatment modalities, along with the starting and stopping of treatment is possible via a user interface 44 coupled to the controller 26, which includes an output or display interface 46, as well as an input interface 48.

Figure 2:
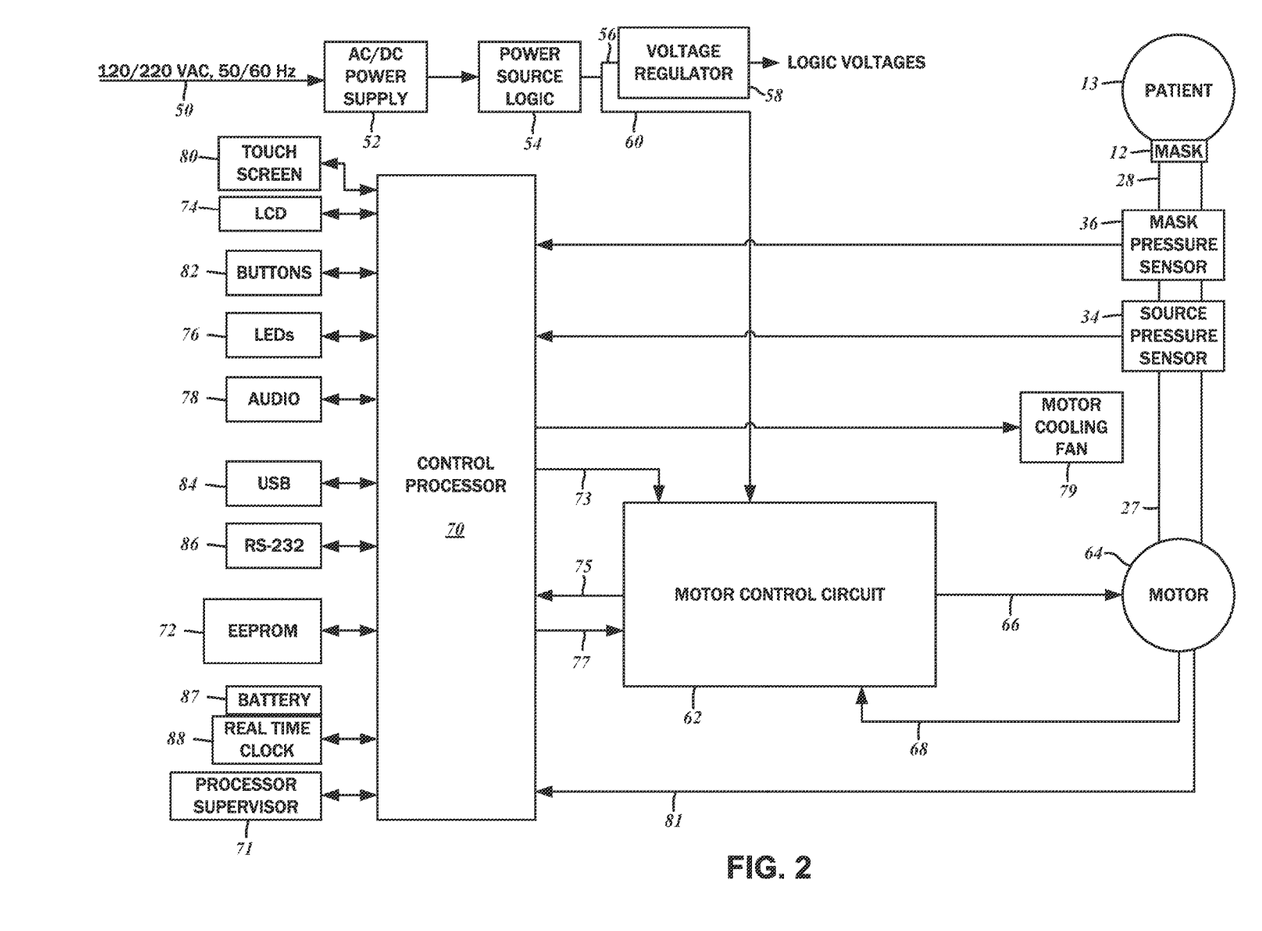
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 50. A power supply 52 is connected to the power source 50, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the ventilation source 22 utilizes a higher DC voltage than control logic devices, and thus the power supply 52 is connected to a power source logic 54. A first output 56 of the power source logic 54 is connected to an integrated circuit voltage regulator 58 that steps down the DC voltage to the logic device level of 5V. A second output 60 of the power source logic 54 is the existing high DC voltage directly from the power supply 52, and is connected to a motor control circuit 62.

The ventilation source 22 is comprised of several electrical components, including a motor 64 and the aforementioned motor control circuit 62. In accordance with one embodiment, the motor 64 is a brushless DC or electrically commutated motor. It will be recognized that the speed of rotation of the motor 64 is based upon input logic signals provided to the motor control circuit 62, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the source pressure sensor 34 and the patient interface pressure sensor 36 are connected to the pneumatic circuit between the motor 64 and the patient 13.

The motor control circuit 62 has a motor drive output 66 that is connected to the motor 64. The rotational position of the motor 64 is detected by a Hall-effect sensor that is incorporated into the motor 64. An output voltage 68 from the Hall-effect sensor is fed back to the motor control circuit 62, which ensures that the actual position corresponds to the intended or commanded position.

The controller 26 and its functionality may be implemented with a programmable integrated circuit device such as a microcontroller or control processor 70. Broadly, the control processor 70 receives certain inputs, and based upon those inputs, generates certain outputs. The specific operations that are performed on the inputs may be programmed as instructions that are executed by the control processor 70. In this regard, the control processor 70 may include an arithmetic/logic unit (ALU), various registers, and input/output ports. Although external memory such as EEPROM (electrically erasable/programmable read only memory) 72 may be connected to the control processor 70 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 70 is powered by a low voltage DC supply from the voltage regulator 58.

As mentioned above, in order to set the operational parameters of the ventilation unit, and to initiate or terminate certain functions, a graphical user interface is provided. Such graphical user interface is generated on a display screen 74, which may be of a liquid crystal display (LCD) type. Any type of graphic may be shown on the display screen 74, though for more specific indicators, a simple light emitting diode (LED) device 76 may be utilized. It will be recognized that alarm conditions, power status, and the like may be indicated with the LED device 76. Audible outputs may also be produced with audio transducers 78 that are likewise connected to the control processor 70. Among the contemplated outputs that may be generated on the audio transducer 78 include simple beeps and alarms, as well as sophisticated voice prompts that provide information and instructions.

An operator may interact with the graphical user interface through different input devices such as a touch screen interface 80 that is overlaid on the display screen 72. It will be recognized that various graphic elements may be generated on the display screen 72, with touch inputs/interactions corresponding in position to those graphic elements being evaluated as a selection or activation of the same. Various touch screen interfaces, some of which may be directly integrated with the display screen 72, are known in the art.

Besides touch screen inputs, buttons 82 may also be connected to the control processor 70 for similarly receiving user inputs. It is understood that the audio transducer 78 may also accept sound input in the form of voice commands, the processing of which is performed may be performed by the control processor 70.

Several modalities for connecting to and communicating with other data processing devices such as general-purpose computers are also contemplated. Accordingly, the control processor 70 may be connected to a universal serial bus (USB) controller 84. For more basic communications, there may be a serial RS-232 transceiver 86. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 70 is connected to a real time clock 88 that maintains a common clock cycle. Although a primary feature of the real time clock 88 is to maintain synchrony at a processor cycle level, longer term time data is also maintained. In order to retain such time data, the real time clock 88 may be powered independently of the primary power source 50, and there is accordingly a battery backup 87. Under heavy processing loads or unexpected program conditions, the control processor 70 may become unable to execute critical programmed steps in real-time. Thus, the control processor 70 may include a processor supervisor 71 that invokes a program execution break upon detecting such conditions. Typically, this is implemented as a step of clearing a memory variable periodically, and when that step is unable to take place because instruction execution is frozen or otherwise delayed, the processor supervisor 71 may cause a predetermined routine to be executed.

As mentioned above, the motor 64 is driven by the motor control circuit 62, which generates different outputs depending on signals received from the control processor 70. The signal to drive the motor 64 is generated on a current command line 73. For control processing on a broader level, feedback from the ventilation source 22 is utilized, and in the specific form of a speed or current measurement input 75 from the motor control circuit 62. Furthermore, as detailed below, pressure readings at the ventilation source 22 and the patient 13 are utilized to reach control decisions. Accordingly, the source pressure sensor 34 and the patient interface pressure sensor 36 are both connected to the control processor 70. The ventilation source 22 is activated and deactivated via a motor enable line 77. To ensure that the temperature of the motor 64 remains within operational parameters, a motor cooling fan 79 may be driven directly by the control processor 70. In some embodiments, there may be additional control circuitry that isolates the power source of the motor cooling fan 79 from the control processor 70. The decision to activate and deactivate the motor cooling fan 79 may be made in response to temperature readings from the motor 64, and so there is a motor temperature reading 81 passed to the control processor 70.

Notwithstanding the foregoing description of the particular respiratory assistance device 10, the contemplated method of operation and a system configured for such operation can be adapted to any other respiratory assistance device 10. Various embodiments of the present disclosure contemplate the selective ramping of therapeutic pressure by the respiratory assistance device 10. Generally, this refers to the gradual increase of pressure to the patient 13 so as to minimize discomfort while transitioning from a wakeful state, where any slight increase in airway pressure is immediately noticeable, to a sleeping state, where the patient airway can be splinted with full prescription pressure without disturbance. The graph of FIG. 3 broadly illustrates the contemplated transitioning of delivered therapeutic gas pressure 89 over time from the moment the respiratory assistance device 10 is activated to the therapy steady-state condition. The X-axis represents time, while the Y-axis represents the pressure level.

Figure 3:
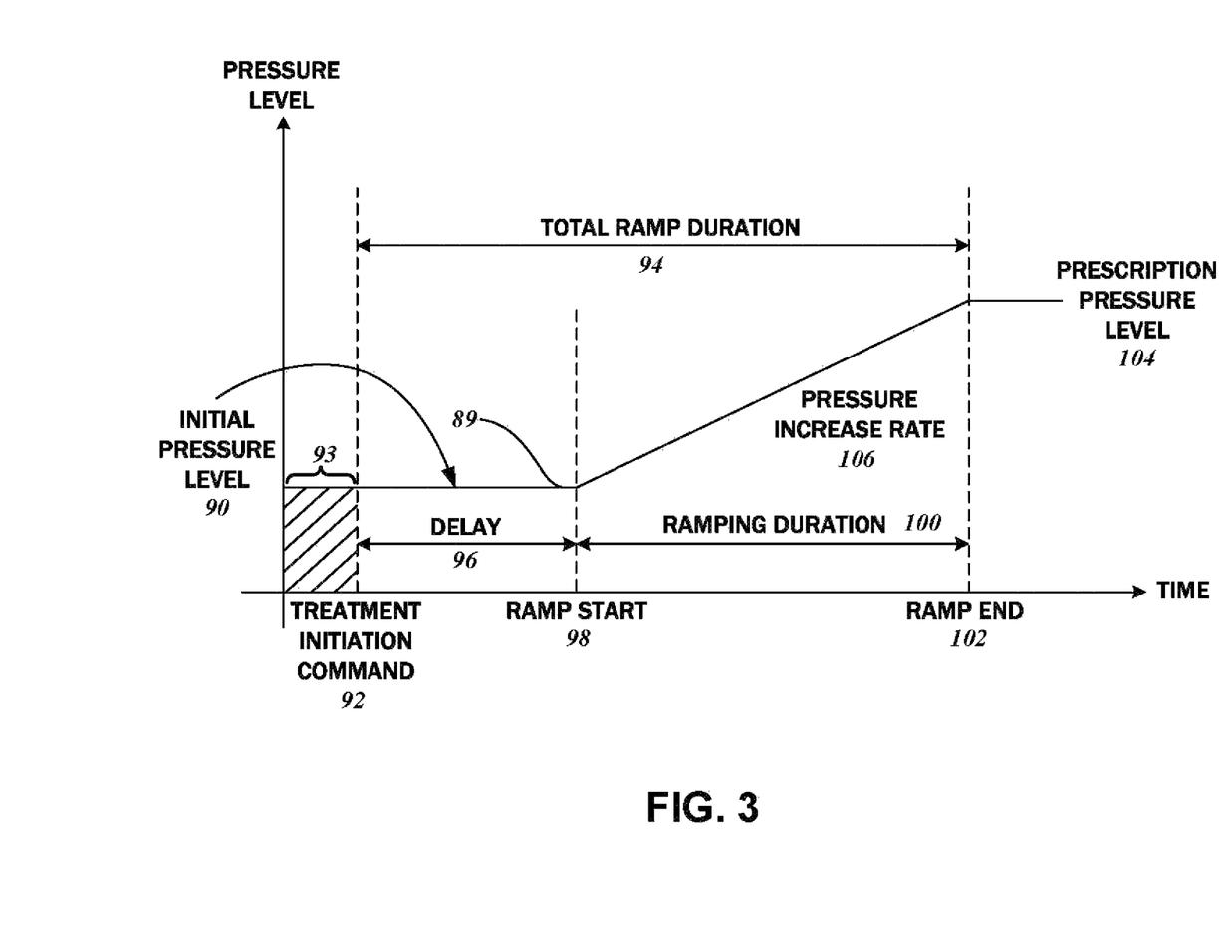
FIG. 3 a graph illustrating a ramped delivery of therapeutic gas delivery to a patient in accordance with one embodiment of the present disclosure.

In accordance with several implementations of the respiratory assistance device 10, the controller 26 accepts various inputs and generates responsive outputs to the ventilation source 22 to carry out the method of selective ramping of the present disclosure. As pertinent to the present disclosure, the controller 26 may also be referred to as a ramp controller. As is the case with any real-time control system, the set points established by the controller 26 for the delivered therapeutic gas pressure 89 at any given instant in time may not necessarily correspond exactly to the true measurement thereof. The graph of FIG. 3 is an illustration of the ideal set points, and accordingly may not represent an actual measured response at the patient ventilation interface 12.

In further detail, the controller 26 is understood to actuate the ventilation source 22 to deliver an initial pressure level 90. As will be discussed more fully below, the initial pressure level 90 may begin in response to a treatment initiation command 92, which is also defined as the beginning point of a total ramp duration 94. Prior to the receipt of the treatment initiation command 92 but subsequent to the activation of the respiratory assistance device 10, the controller 26 may actuate the ventilation source 22 to deliver an indeterminate pressure level 93. In most cases, this will be lower than the initial pressure level 90, and likely maintained at or near zero. The initial pressure level 90 is maintained for a ramp delay 96, which is understood to correspond to the estimated or anticipated time for which the patient 13 to enter the sleeping state. At the end of the ramp delay 96, which is also defined as a ramp start point 98, the controller 26 is understood to increase the delivered therapeutic gas pressure 89 over a ramping duration 100, which concludes at a ramp end point 102 that coincides with the end of the total ramp duration 94. The delivered therapeutic gas pressure 89 is increased to a prescription pressure level 104, where it is maintained until the end of therapy or other exit condition.

The ramp delay 96 is contemplated to be user-adjustable, but is subject to the limitations imposed by the pre-defined total ramp duration 94. This is also understood to affect the ramping duration 100, and depending on the initial pressure level 90 and the prescription pressure level 104, the slope of the therapeutic gas pressure delivery 89 between the ramp start 98 and the ramp end 102, i.e., a pressure increase rate 106, may likewise be modified.

Figure 4:
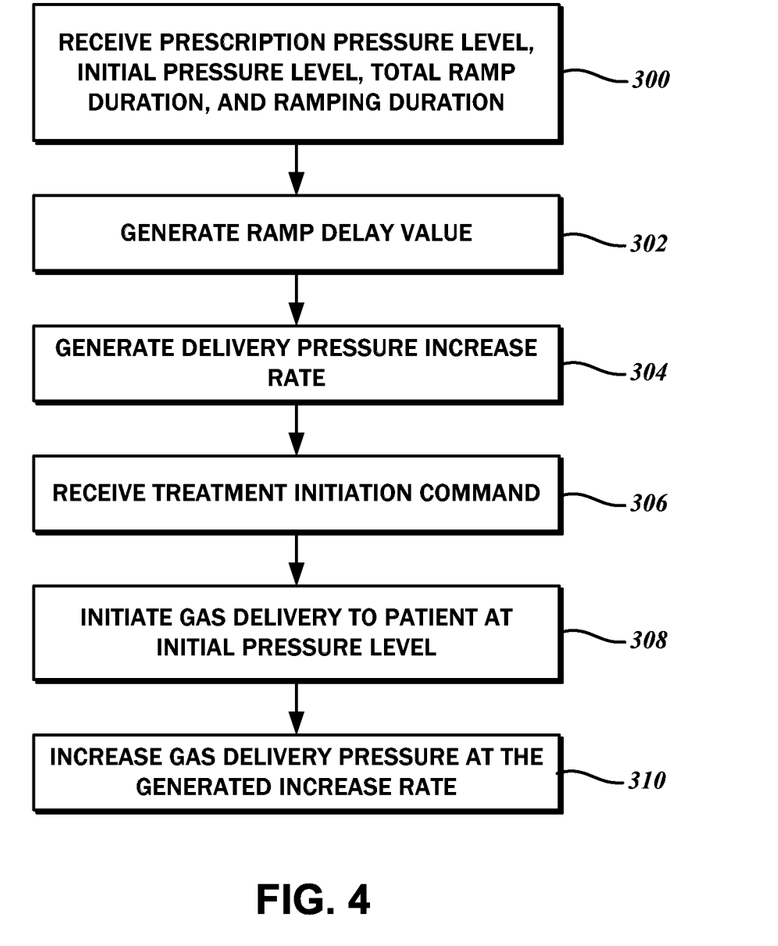
FIG. 4 is a flowchart depicting one method for selective ramping of therapeutic gas delivery.

Referring now to the flowchart of FIG. 4, additional details pertaining to the method of selective ramping, with which the foregoing response of the delivered therapeutic gas pressure 89 can be realized with the respiratory assistance device 10, will be considered. The method may begin with a step 300 of receiving the prescription pressure level 104, the initial pressure level 90, the total ramp duration 94, and the numeric value corresponding to the ramping duration 100. These values may be specified by skilled medical personnel and entered into the respiratory assistance device 10 by the patient 13. In most cases, the prescription pressure level 104 and the initial pressure level 90 will be set more or less permanently, with the option to modify such operational parameters being minimal. The user interface 44, also referred to as a user interface module, may be used to enter these values.

In comparison to the initial pressure level 90 and the prescription pressure level 104, the total ramp duration 94 and the ramping duration 100 is more likely to be adjusted by the patient 13, and accordingly, the interface to modify these values are presented in a more accessible fashion. After activating the respiratory assistance device 10 but before initiating therapy, the patient 13 can be presented with an interface to enter the total ramp duration 94. One possible interface is shown in co-pending U.S. patent application Ser. No. 13/524,983 filed Jun. 15, 2012 and entitled "METHOD AND SYSTEM FOR OPERATING A PATIENT VENTILATION DEVICE," the entirety of the disclosure of which is incorporated by reference herein.

One of the contemplated ways in which the ramping duration 100 may be specified is as a relative percentage or proportion of the total ramp duration 94. More particularly, the ramp percentage may be defined as the percentage of the ramping duration 100 over the total ramp duration 94, i.e., % Ramp=(Ramping Duration)×100/(Total Ramp Duration). For example, if a 50% ramp is specified for a total ramp duration 94 of twenty minutes, then the ramp time is understood to be ten minutes, with a ramp delay 96 of also ten minutes. The generation of the specific time value of the ramp delay 96 for countdown purposes by the controller 26 takes place in another step in the method, and will be discussed more fully below.

Figure 5A:
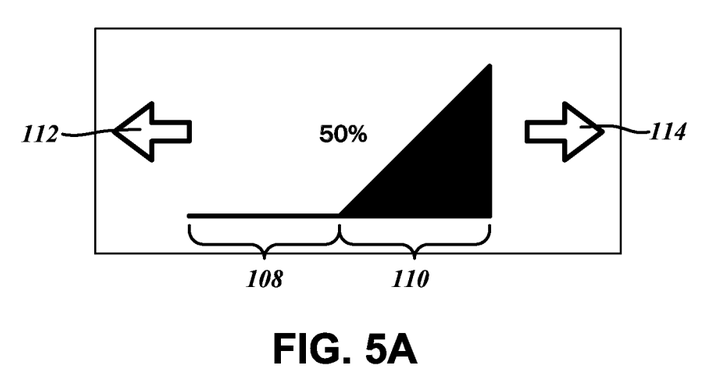
FIG. 5A-5C are graphs comparatively illustrating various delivery pressure increase or ramping rates and as could be further displayed on an interactive graphical user interface for setting and adjustment of the same.
Figure 5B:
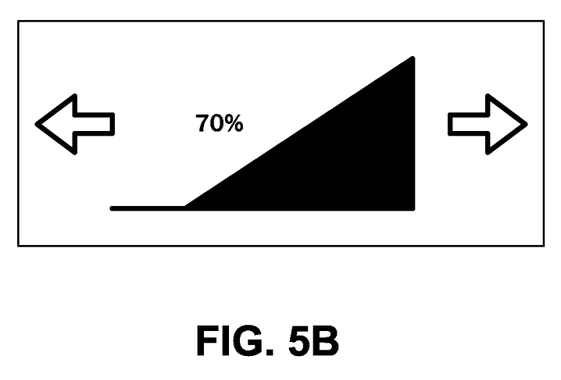
Figure 5C:
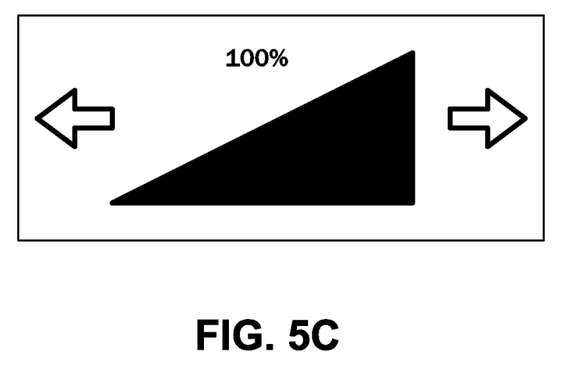

An exemplary user interface for specifying the ramping duration 100 in this fashion is shown in FIGS. 5A-5C, which is represented by a graphic that depicts its relationship to the ramp delay 96. More particularly, the ramp delay 96 is shown as a flat portion 108, while the ramping duration 100 is shown as an angled wedge portion 110, the combination of which is understood to represent the total ramp duration 94. The user interface of FIG. 5A shows the aforementioned example 50% delay, with the flat portion 108 and the angled wedge portion 110 being the same length. Actuating a first user interface element 112, which is a left-pointing arrow, may be operative to decrement the ramp delay 96 and increment the ramping duration 100. Alternatively, actuating a second user interface element 114, which is a right-pointing arrow, may be operative to increment the ramp delay 96 and decrement the ramping duration 100. It will be recognized by those having ordinary skill in the art that each actuation of the first user interface element 112 or the second user interface element 114 may be effectuate a change of an arbitrary amount or increment. In some cases, each increment may be as small as 5%, though it may also be as large as 25%. Following the input of modifying the ramp delay 96 in accordance with the foregoing, the user interface of FIG. 5B represents a 70% ramping duration 100, or a 30% ramp delay 96, while the user interface of FIG. 5C represents a 100% ramping duration 100, or a 0% ramp delay 96.

Other user interfaces besides those mentioned above to specify the numeric value of the ramping duration 100 may be substituted without departing from the present disclosure. For instance, the raw percentage values may be keyed numerically. Furthermore, beyond the specifying of the ramping duration 100 in terms of a percentage of the total ramp duration 94, it may also be specified in time units such as seconds, minutes, and so forth.

The length of time of the ramp delay 96 is generated in a step 302. In the foregoing embodiment in which the corresponding numeric value of the ramping duration 100 is specified in terms of percentages, the ramp delay 96 is understood to be the reciprocal value of the ramping duration 100 relative to the total ramp duration 94. The ramp delay 96 is a product of the total ramp duration 94 and the reciprocal remainder of the decimal equivalent of the ramping duration percentage, per the examples shown above. Thus, in the case of a 70% ramp, the ramp delay 96 is given by (1-0.7)×Total Ramping Duration. Although described herein with only two terms, i.e., the ramp delay 96 and the corresponding ramping duration 100 relative to the total ramp duration 94, it is also contemplated that other terms may be introduced that either subtract from or add to either of these existing terms in various ways.

With the ramp delay 96 and the ramping duration 100 being set, the method continues with a step 304 of generating the pressure increase rate 106. As indicated above, one embodiment involves the linear increase of the delivered therapeutic gas pressure 89 from the ramp start 98 to the ramp end 102. At the ramp start 98, the delivered therapeutic gas pressure 89 is understood to be the initial pressure level 90, while at the ramp end 102, it is understood to be the prescription pressure level 104. As will be readily recognized by those having ordinary skill in the art, the slope or the pressure increase rate 106 is the quotient of the remainder of the initial pressure level 90 subtracted from the prescription pressure level 104 and the remainder of the ramp start point 98 subtracted from the ramp end point 102. Again, as is the case with the generating of the ramp delay 96, the generating of the pressure increase rate 106 may also involve additional terms that can account for environmental variables/conditions or employ different mathematical functions besides the example linear function such as logarithmic functions and exponential functions. Nothing herein is intended to limit the respiratory assistance device 10 to the foregoing specifics.

The foregoing calculations of the ramp delay 96 value in step 302 and the delivery pressure increase rate 106 in step 304 may occur before initiating any treatment, or on-the-fly, depending on whether such calculations utilize real-time measurements for further refinement in operation. In embodiments where the calculations occur once the requisite values are set and before treatment, the method continues with a step 306 of receiving the treatment initiation command 92. It is expressly contemplated that treatment can be started automatically upon a detection of certain pre-requisite conditions being satisfied therefor, namely, the pneumatic connection of the patient ventilation interface 12 to the patient 13 and to the ventilation unit 14. When this condition is satisfied, spontaneous patient respiration may be detected by the patient interface pressure sensor 36, for example. This information can then be translated to the treatment initiation command 92. Alternatively, the treatment initiation command 92 may be an input received from the patient 13 via the user interface component 65 indicating the request to start treatment, without any confirmation by the controller 26 that the patient airway circuit is complete. Further still, a combination of the foregoing features is also expressly contemplated.

The method continues with a step 308 of initiating gas delivery to the patient 13 at the initial pressure level 90 in response to the treatment initiation command 92. The gas delivery at the initial pressure level 90 continues for the duration of the ramp delay 96 generated in step 302. As briefly discussed above, the intended set point of the therapeutic gas pressure 89 may slightly deviate from the actual delivered therapeutic gas pressure in part due to different environmental conditions, delays, and so forth. Therefore, the pressure at the patient ventilation interface 12 is compared against the desired set point for that particular time instant as governed by the ramp delay value 96. To the extent that any significant deviation is detected, the controller 26 may direct the ventilation source 22 accordingly to shift the pressure at the patient 13 closer to the intended set point. These comparisons may occur at a predetermined rate, and in accordance with one embodiment of the present disclosure, this may be one hundred times a second, or 100 Hz. This sampling rate may be varied depending on the data processing capabilities of the controller 26. Broadly, a feedback control modality is envisioned for regulating the delivered therapeutic gas pressure.

Upon expiration of the ramp delay 96, the method proceeds to a step 310 which includes increasing the delivery of the therapeutic gas pressure 89 to the patient 13 in accordance with the pressure increase rate 106 generated in step 304. Here, as before, a feedback control modality is utilized to keep the actual delivered therapeutic gas pressure to that as defined in the set points per the pressure increase rate 106. When the therapeutic gas pressure 89 matches the preset prescription pressure level 104 and/or the ramping duration 100 and the total ramp duration 94 has elapsed, the respiratory assistance device 10 continues gas delivery at the prescription pressure level 104 until the end of treatment.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. In a respiratory assistance device, a method for selective ramping of therapeutic gas delivery over a first conduit to a patient interface configured for fitment on a patient respiratory passageway, the patient interface including a ventilation mask, the method comprising:

setting operational parameters of a ventilation unit of the respiratory assistance device, the ventilation unit including a blower for generating a gas flow in the first conduit, the operational parameters including a prescription pressure level, an initial pressure level, a total ramp duration defined from a treatment initiation command to a ramp end point, and a ramping duration defined from a ramp start point to the ramp end point, wherein a ramp delay is defined from the treatment initiation command to the ramp start point;

generating a graphical user interface including a screen that allows a user of the respiratory assistance device to modify the ramp delay and the ramping duration without modifying the total ramp duration, the screen including a graphic that depicts a relationship between the ramping duration and the total ramp duration;

generating, on a ramping controller of the respiratory assistance device, the ramp delay value from the ramping duration relative to the total ramp duration;

generating, on the ramping controller of the respiratory assistance device, a delivery pressure increase rate between the initial pressure level and the prescription pressure level based upon a ramp start time and a ramp end time further derived from the ramping duration and the total ramp duration;

receiving a first pressure measurement at the blower, the first pressure measurement being received from a first sensor in line with the first conduit;

receiving a treatment initiation command, the treatment initiation command being generated in response to a sequence of second pressure measurements received on a second sensor disposed within the ventilation unit in fluid communication with the ventilation mask over a second conduit at the mask, the sequence of second pressure measurements being indicative of satisfaction of a first condition followed by satisfaction of a second condition, the first condition being the pneumatic connection of the patient interface to the patient and to the ventilation unit, the second condition being spontaneous patient respiration;

initiating therapeutic gas delivery from the ventilation unit through the first conduit to the ventilation mask at the initial pressure level in response to receiving the treatment initiation command, the therapeutic gas delivery at the initial pressure level continuing for a duration corresponding to the ramp delay value; and increasing gas pressure from the respiratory assistance device to the ventilation mask at the derived delivery pressure increase rate from the ramp start time to reach the prescription pressure level by approximately the ramp end time.

2. The method of claim 1, wherein the ramping duration is specified as a relative percentage of the total ramp duration.

3. The method of claim 1, wherein the ramping duration is specified as a time constant.

4. The method of claim 1, further comprising:
maintaining therapeutic gas pressure at the prescription pressure level subsequent to an expiration of the total ramp duration.

5. The method of claim 1, wherein therapeutic gas pressure at the patient interface is compared against a pressure set point for a time instant as governed by a function of one of the ramp delay value and the delivery pressure increase rate.

6. The method of claim 5, further comprising:
adjusting the therapeutic gas delivery by the respiratory assistance device in response to the comparison of the pressure at the patient interface and the pressure set point for the time instant to subsequently shift the pressure at the patient closer to the pressure set point.

7. The method of claim 5, wherein the comparison of the pressure at the patient interface and the pressure set point occurs at a predefined sampling rate.

8. The method of claim 1, wherein the patient interface further includes a piloted exhalation valve coupled to the ventilation mask.

9. The method of claim 1, further comprising a purge solenoid being in pneumatic communication with the first conduit and the second conduit and configured to deliver a purge flow to clear the second conduit.

10. The method of claim 1, wherein the graphic includes a flat portion representing the ramp delay and an angled wedge portion representing the ramping duration, with a combination of the flat portion and the angled wedge portion representing the total ramp duration.

11. A respiratory assistance device for a patient, comprising:

a patient interface for coupling to a patient respiratory passageway, the patient interface including a ventilation mask;

a selectively regulated therapeutic gas flow source in pneumatic communication with the patient interface over a first conduit, the therapeutic gas flow source including a blower for generating a gas flow in the first conduit;

a first sensor in line with the first conduit for reading gas delivery measurements therefrom, wherein the gas delivery measurements include a first pressure measurement at the blower;

a ramping controller connected to the therapeutic gas flow source and receptive to inputs of a prescription pressure level, an initial pressure level, a total ramp duration defined from a treatment initiation command to a ramp end point, and a ramping duration defined from a ramp start point to the ramp end point, wherein a ramp delay is defined from the treatment initiation command to the ramp start point, the ramping controller generating a graphical user interface including a screen that allows a user of the respiratory assistance device to modify the ramp delay and the ramping duration without modifying the total ramp duration, the screen including a graphic that depicts a relationship between the ramping duration and the total ramp duration, the ramping controller regulating therapeutic gas flow at an initial pressure level for the ramp delay duration, the ramp delay duration being the reciprocal value of the ramping duration relative to the total ramp duration, and incrementally increasing the therapeutic gas flow to the prescription pressure level from a ramp start time to a ramp end time at a delivery pressure increase rate derived from the ramping duration and the total ramp duration; and a second sensor in fluid communication with the ventilation mask over a second conduit for a second pressure measurement at the ventilation mask, wherein the second sensor is connected to the ramping controller, wherein, the ramping controller begins regulating therapeutic gas flow from the therapeutic gas flow source to the ventilation mask at an initial pressure level in response to a treatment initiation command generated in response to a sequence of second pressure measurements received on the second sensor disposed within the ventilation unit in fluid communication with the ventilation mask over the second conduit at the mask, the sequence of second pressure measurements being indicative of satisfaction of a first condition followed by satisfaction of a second condition, the first condition being the pneumatic connection of the patient interface to the patient and to the ventilation unit, the second condition being spontaneous patient respiration.

12. The respiratory assistance device of claim 11, further comprising a display device on which the graphical user interface is generated and at least one user-activatable input button.

13. The respiratory assistance device of claim 11, wherein the ramping duration is a relative percentage of the total ramp duration.

14. The respiratory assistance device of claim 11, wherein the ramping duration is specified as a time constant.

15. The respiratory assistance device of claim 11, wherein therapeutic gas pressure at the ventilation mask measured by the second sensor is compared against a pressure set point for a time instant as governed by a function of the delivery pressure increase rate, any deviations from the pressure set point being fed back to the ramping controller for subsequently adjusting therapeutic gas delivery.

16. The respiratory assistance device of claim 11, further comprising a purge solenoid in pneumatic communication with the first conduit and the second conduit and configured to deliver a purge flow to clear the second conduit.

17. An article of manufacture comprising a program storage medium readable by a data processing apparatus, the program storage medium tangibly embodying one or more programs of instructions executable by the data processing apparatus to perform, in a respiratory assistance device, a method for selective ramping of therapeutic gas delivery over a first conduit to a patient interface configured for fitment on a patient respiratory passageway, the patient interface including a ventilation mask, the one or more programs of instructions, when executed, cause the respiratory assistance device to perform operations comprising:

setting operational parameters of a ventilation unit of the respiratory assistance device, the ventilation unit including a blower for generating a gas flow in the first conduit, the operational parameters including a prescription pressure level, an initial pressure level, a total ramp duration defined from a treatment initiation command to a ramp end point, and a ramping duration defined from a ramp start point to the ramp end point, wherein a ramp delay is defined from the treatment initiation command to the ramp start point;

generating a graphical user interface including a screen that allows a user of the respiratory assistance device to modify the ramp delay and the ramping duration without modifying the total ramp duration, the screen including a graphic that depicts a relationship between the ramping duration and the total ramp duration;

generating, on a ramping controller of the respiratory assistance device, the ramp delay value from the ramping duration relative to the total ramp duration;

generating, on the ramping controller of the respiratory assistance device, a delivery pressure increase rate between the initial pressure level and the prescription pressure level based upon a ramp start time and a ramp end time further derived from the ramping duration and the total ramp duration;

receiving a first pressure measurement at the blower, the first pressure measurement being received from a first sensor in line with the first conduit;

receiving a treatment initiation command, the treatment initiation command being generated in response to a sequence of second pressure measurements received on a second sensor disposed within the ventilation unit in fluid communication with the ventilation mask over a second conduit at the mask, the sequence of second pressure measurements being indicative of satisfaction of a first condition followed by satisfaction of a second condition, the first condition being the pneumatic connection of the patient interface to the patient and to the ventilation unit, the second condition being spontaneous patient respiration;

initiating therapeutic gas delivery from the ventilation unit through the first conduit to the ventilation mask at the initial pressure level in response to receiving the treatment initiation command, the therapeutic gas delivery at the initial pressure level continuing for a duration corresponding to the ramp delay value; and increasing therapeutic gas pressure from the respiratory assistance device to the mask at the derived delivery pressure increase rate from the ramp start time to reach the prescription pressure level by approximately the ramp end time.

18. The article of manufacture of claim 17, wherein the ramping duration is specified as a relative percentage of the total ramp duration.

19. The article of manufacture of claim 17, wherein the ramping duration is specified as a time constant.

20. The article of manufacture of claim 17, further comprising a purge solenoid being in pneumatic communication with the first conduit and the second conduit and configured to deliver a purge flow to clear the second conduit.

* * * * *